United States Patent [19]

Kung et al.

[11] 4,363,799

[45] Dec. 14, 1982

[54] MONOCLONAL ANTIBODY TO HUMAN T CELLS, AND METHODS FOR PREPARING SAME

[75] Inventors: Patrick C. Kung, Bridgewater; Gideon Goldstein, Short Hills, both of N.J.

[73] Assignee: Ortho Pharmaceutical Corporation, Raritan, N.J.

[21] Appl. No.: 22,132

[22] Filed: Mar. 20, 1979

[51] Int. Cl.$^3$ ............ A61K 39/395; C12N 5/00; C12N 5/02; C12N 15/00; C12Q 1/00; G01N 33/48; G01N 33/68; G01N 33/96

[52] U.S. Cl. .................... 424/85; 260/112 R; 424/101; 424/177; 435/7; 435/172; 435/240; 435/241; 436/548

[58] Field of Search ............ 424/8, 12, 85, 101, 424/177; 260/112 R; 435/172, 240, 241

[56] References Cited

U.S. PATENT DOCUMENTS 4,172,124 10/1979 Koprowski ............ 424/85
4,196,265 4/1980 Koprowski ............ 424/85
4,284,412 8/1981 Hansen ............ 23/230 B

OTHER PUBLICATIONS

Kennett, SSIE Ab 1CA 189303, HEW Grant 1977-1979.
Herzenberg, SSIE Ab, 1CA 4681-20, HEW Grant 1977-1979.
Reinherz et al., J. Immunol. vol. 123, 1979, pp. 1312-1317.
Reinherz et al., Proc. Nat. Acad. Sci., vol. 76, 1979, pp. 4061-4065.
Kung et al., Sci., vol. 206, 1979, pp. 347-349.
Williams, Cell, vol. 12, 1977, pp. 663-673.
Friedman, Immunology, vol. 31, 1976, pp. 759-765.
Bobbrove, J. of Immunology, vol. 112, 1974, pp. 520-527.
Brochier, Immunology, vol. 31, 1976, pp. 749-758.
McMichael, Eur. J. Immunol., vol. 9, 1979, pp. 205-210.
Lampson, J. of Supramolecular Structure, vol. 6, 1977, pp. 441-448.
Melchers (Ed) Lymph, Hybridoms, 2nd, Workshop on Functional Properties of Tumors of T&B Lymph; Springer Verlag, Berlin/NY 1978, pp. IX-XVIII.
Yelton, et al, Supra, pp. 1-7.
Trucco et al, Supra, pp. 66-69.
Levy et al, Supra, pp. 164-169.
Hammerling et al, Supra, pp. 100-106.
Iverson, et al, Supra, pp. 192-194.
Simpson et al, Supra, pp. 195-202.
Ruddle, Supra, pp. 203-211.
Taniguchi et al, Supra, pp. 212-216.
Osborne et al, Supra, pp. 217-220.
Saravia et al, Supra, pp. 224-231.
Fox, C&E News, Jan. 1, 1979, pp. 15-17.
White et al, J. Exp. Med., vol. 148, Sep. 1, 1978, pp. 664-673.
Herzenberg et al, from Wier (ED) Handbook of Exptl. Immunol., Blackwell, London, 3rd Ed, 1978, pp. 25.1-25.7.

Primary Examiner—Anna P. Fagelson
Attorney, Agent, or Firm—Geoffrey G. Dellenbaugh

[57] ABSTRACT

Hybrid cell line for production of monoclonal antibody to an antigen found on all normal human T cells. The hybrid is formed by fusing splenocytes from immunized Balb/cJ mice with P3X63Ag8U1 myeloma cells. Diagnostic and therapeutic uses of the monoclonal antibody are also disclosed.

11 Claims, 5 Drawing Figures

Fig. 3.

T-ALL  T-CLL

CELL NUMBER

FLUORESCENSE INTENSITY

Fig. 4.

HJD-1  CEM  HSB-2

CELL NUMBER

FLUORESCENCE INTENSITY

Fig. 5.

B-LYMPHOBLASTOID LINE

CELL NUMBER

FLUORESCENCE INTENSITY

MONOCLONAL ANTIBODY TO HUMAN T CELLS, AND METHODS FOR PREPARING SAME

FIELD OF THE INVENTION

This invention relates generally to new hybrid cell lines and more specifically to hybrid cell lines for production of monoclonal antibody to an antigen found on all normal human T cells, to the antibody so produced, and to therapeutic and diagnostic methods employing this antibody.

DESCRIPTION OF THE PRIOR ART

The fusion of mouse myeloma cells to spleen cells from immunized mice by Kohler and Milstein in 1975 [Nature 256, 495–497 (1975)] demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. See, for example, *Current Topics in Microbiology and Immunology*, Volume 81 - "Lymphocyte Hybridomas", F. Melchers, M. Potter, and N. Warner, Editors, Springer-Verlag, 1978, and references contained therein; C. J. Barnstable, et al., *Cell*, 14, 9–20 (May, 1978); P. Parham and W. F. Bodmer, *Nature* 276, 397–399 (November, 1978); *Handbook of Experimental Immunology*, Third Edition, Volume 2, D. M. Wier, Editor, Blackwell, 1978, Chapter 25; and *Chemical and Engineering News*, January 1, 1979, 15–17.

These references simultaneously indicate the rewards and complications of attempting to produce monoclonal antibody from hybridomas. While the general technique is well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

The attempted production of monoclonal antibody to human lymphocyte cell-surface antigens has been reported only in a few instances. See, for example, *Current Topics in Microbiology and Immunology*, ibid, 66–69 and 164–169. The antigens used in these reported experiments were cultured human lymphoblastoid leukemia and human chronic lymphocytic leukemia cell lines. Many hybridomas obtained appeared to produce antibody to various antigens on all human cells. None of the hybridomas produced antibody against a predefined class of human lymphocytes.

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system. The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively) promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221-232, 1977; and L. Chess and S. F. Schlossman—"Functional Analysis of Distinct Human T-Cell Subsets Bearing Unique Differentiation Antigens", in "*Contemporary Topics in Immunobiology*", O. Stutman, Editor, Plenum Press, 1977, Volume 7, 363–379.

The ability to identify or suppress classes or subclasses of T cells is important for diagnosis or treatment of various immunoregulatory disorders or conditions.

For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58:300 (March, 1975); D. Belpomme, et al., in "*Immunological Diagnosis of Leukemias and Lymphomas*", S. Thierfelder, et al., eds, Springer, Heidelberg, 1977, 33–45; and D. Belpomme, et al., *British Journal of Haematology*, 1978, 38, 85. Certain diseases states (e.g., juvenile rheumatoid arthritis and certain leukemias) are associated with an imbalance of T cell subclasses. It has been suggested that autoimmune diseases generally are associated with an excess of "helper" T cells or a deficiency of certain "suppressor" T cells, while malignancies generally are associated with an excess of "suppressor" T cells. In certain leukemias, excess T cells are produced in an arrested stage of development. Diagnosis may thus depend on the ability to detect this imbalance or excess. See, for example, J. Kersey, et al., "Surface Markers Define Human Lymphoid Malignancies with Differing Prognoses" in *Haematology and Blood Transfusion*, Volume 20, Springer-Verlag, 1977, 17–24, and references contained therein.

On the therapeutic side, there is some suggestion, as yet not definitely proven, that administration of antibodies against the subtype of T cell in excess may have therapeutic benefit in autoimmune disease or malignancies. Antisera against the entire class of human T cells (so-called antihuman thymocyte globulin or ATG) has been reported useful therapeutically in patients receiving organ transplants. Since the cell-mediated immune response (the mechanism whereby transplants are rejected) depends upon T cells, administration of antibody to T cells prevents or retards this rejection process. See, for example, Cosimi, et al., "Randomized Clinical Trial of ATG in Cadaver Renal Allgraft Recipients: Importance of T Cell Monitoring", *Surgery* 40:155-163 (1976) and references contained therein.

The identification and suppression of human T cell classes and subclasses has previously been accomplished by the use of spontaneous antoantibodies or selective antisera for human T cells obtained by immunizing animals with human T cells, bleeding the animals to obtain serum, and adsorbing the antiserum with (for example) autologous but not allogeneic B cells to remove antibodies with unwanted reactivities. The preparation of these antisera is extremely difficult, particularly in the adsorption and purification steps. Even the adsorbed and purified antisera contain many impurities in addition to the desired antibody, for several reasons. First, the serum contains millions of antibody molecules even before the T cell immunization. Second, the immunization causes production of antibodies against a variety of antigens found on all human T cells injected. There is no selective production of antibody against a single antigen. Third, the titer of specific antibody obtained by such methods is usually quite low, (e.g., inactive at dilutions greater than 1:100) and the ratio of specific to non-specific antibody is less than $1/10^6$.

See, for example, the Chess and Schlossman article referred to above (at pages 365 and following) and the Chemical and Engineering News article referred to above, where the deficiencies of prior art antisera and the advantages of monoclonal antibody are described.

SUMMARY OF THE INVENTION

There has now been discovered a novel hybridoma which is capable of producing novel monoclonal antibody against an antigen found on essentially all normal human peripheral T cells. The antibody so produced is monospecific for a single determinant on normal human T cells and contains essentially no other anti-human immuneglobulin, in contrast to prior art antisera (which are inherently contaminated with antibody reactive to numerous human antigens) and to prior art monoclonal antibodies (which are not monospecific for a human T cell antigen). Moreover, this hybridoma can be cultured to produce antibody without the necessity of immunizing and killing animals, followed by the tedious adsorption and purification steps necessary to obtain even the impure antisera of the prior art.

It is accordingly one object of this invention to provide hybridomas which produce antibodies against an antigen found on essentially all normal human T cells.

It is a further aspect of the present invention to provide methods for preparing these hybridomas.

A further object of the invention is to provide essentially homogeneous antibody against an antigen found on essentially all normal human T cells.

A still further object is to provide methods for treatment or diagnosis of disease employing these antibodies.

Other objects and advantages of the invention will become apparent from the examination of the present disclosure.

In satisfaction of the foregoing objects and advantages, there is provided by this invention a novel hybridoma producing novel antibody to an antigen found on essentially all normal human T cells, the antibody itself, and diagnostic and therapeutic methods employing the antibody. The hybridoma was prepared generally following the method of Milstein and Kohler. Following immunization of mice with normal E rosette positive human T cells, the spleen cells of the immunized mice were fused with cells from a mouse myeloma line and the resultant hybridomas screened for those with supernatants containing antibody which gave selective binding to normal E rosette positive human T cells. The desired hybridomas were subsequently cloned and characterized. As a result, a hybridoma was obtained which produces antibody (designated OKT1) against an antigen on essentially all normal human T cells. Not only does this antibody react with essentially all normal human peripheral T cells, but it also does not react with other normal peripheral blood lymphoid cells. In addition, the cell surface antigen recognized by this antibody is detected on only mature thymocytes and is completely lacking on greater than 90% of normal human thymocytes.

In view of the difficulties indicated in the prior art and the lack of success reported using malignant cell lines as the antigen, it was surprising that the present method provided the desired hybridoma. It should be emphasized that the unpredictable nature of hybrid cell preparation does not allow one to extrapolate from one antigen or cell system to another. In fact, the present applicants have discovered that using a T cell malignant cell line as the antigen caused formation of hybridomas which did not produce the desired antibody. Attempts to use purified antigens separated from the cell surfaces were also unsuccessful.

The preparation and characterization of the hybridoma and the resultant antibody will be better understood by reference to the following description and Examples.

DETAILED DESCRIPTION OF THE INVENTION

The method of preparing the hybridoma generally comprises the following steps:

A. Immunizing mice with E rosette positive purified normal human peripheral T cells. While it has been found that female Balb/cJ mice are preferred, it is contemplated that other mouse strains could be used. The immunization schedule and T cell concentration should be such as to produce useful quantities of suitably primed splenocytes. Three immunizations at fourteen day intervals with $2\times 10^7$ cells/mouse/injection in 0.2 ml phosphate buffered saline has been found to be effective.

B. Removing the spleens from the immunized mice and making a spleen suspension in an appropriate medium. About one ml of medium per spleen is sufficient. These experimental techniques are well-known.

C. Fusing the suspended spleen cells with mouse myeloma cells from a suitable cell line by the use of a suitable fusion promoter. The preferred ratio is about 5 spleen cells per myeloma cell. A total volume of about 0.5-1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, Calif. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, the mixture of unfused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1-4) in each separate container (e.g., each well of a microtiter plate). The medium is one (e.g., HAT medium) which will not support the drug-resistant (e.g., 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to reproduce. The fused cells, on the other hand, continue to reproduce because they possess the malignant quality of the myeloma parent and the ability to survive in the selective medium of the spleen cell parent.

E. Evaluating the supernatant in each container (well) containing a hybridoma for the presence of antibody to E rosette positive purified human T cells.

F. Selecting (e.g., by limiting dilution) and cloning hybridomas producing the desired antibody.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 $\mu$g/ml.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested ascites or from the serum is essentially free of any contaminating antihuman immune globulin. This monoclonal antibody is high titer (active at dilutions of 1:30,000 or higher) and high ratio of specific to non-specific immune globulin (about 1/20). Immune globulin produced incorporating the $\kappa$ light myeloma chains are non-specific, "nonsense" peptides which merely dilute the monoclonal antibody without detracting from its specificity.

EXAMPLE I

Production of Monoclonal Antibodies

A. Immunization and Somatic Cell Hybridization

Female Balb/cJ mice (Jackson Laboratories; 6-8 weeks old) were immunized intraperitoneally with $2\times10^7$ E rosette purified T cells in 0.2 ml of phosphate buffered saline at 14-day intervals. Four days after the third immunization, spleens were removed from the mice, and a single cell suspension was made by pressing the tissue through a stainless steel mesh.

Cell fusion was carried out according to the procedure developed by Kohler and Milstein. $1\times10^8$ splenocytes were fused in 0.5 ml of a fusion medium comprising 35% polyethylene glycol (PEG 1000) and 5% dimethylsulfoxide in RPMI 1640 medium (Gibco, Grand Island, N.Y.) with $2\times10^7$ P3X63Ag8U1 myeloma cells supplied by Dr. M. Scharff, Albert Einstein College of Medicine, Bronx, N.Y. These myeloma cells secrete IgG$_1$ $\kappa$ light chains.

B. Selection and Growth of Hybridoma

After cell fusion, cells were cultured in HAT medium (hypoxanthine, aminopterin, and thymidine) at 37° C. with 5% CO$_2$ in a humid atmosphere. Several weeks later, 40 to 100 $\mu$l of supernatant from cultures containing hybridomas were added to a pellet of $10^6$ peripheral lymphocytes separated into E rosette positive (E+) and E rosette negative (E−) populations, which were prepared from blood of healthy human donors as described by Mendes (J. Immunol. 111:860, 1973). Detection of mouse hybridoma antibodies binding to these cells was determined by radioimmunoassay and/or indirect immunofluorescence. In the first method, the cells were initially reacted with 100 $\mu$l of affinity-purified $^{125}$I goat-anti-mouse IgG ($10^6$ cpm/$\mu$g; 500 $\mu$g/$\mu$l). (Details of iodination of goat-anti-mouse were described by Kung, et al., J. Biol. Chem. 251(8):2399, 1976). Alternatively, cells incubated with culture supernatants were stained with a fluorescinated goat-anti-mouse IgG (G/M FITC) (Meloy Laboratories, Springfield, Va.; F/p=2.5) and the fluorescent antibody-coated cells were subsequently analyzed on the Cytofluorograf FC200/4800A (Ortho Instruments, Westwood, MA) as described in Example III. Hybridoma cultures containing antibodies reacting specifically with E$^{30}$ lymphocytes (T cells) were selected and cloned. Subsequently, the clones were transferred intraperitoneally by injecting $1\times10^7$ cells of a given clone (0.2 ml volume) into Balb/cJ mice primed with 2,6,10,14-tetramethylpentadecane, sold by Aldrich Chemical Company under the name Pristine. The malignant ascites from these mice were then used to characterize lymphocytes as described below in Example II. The subject hybrid antibody OKT1 was demonstrated by standard techniques to be of IgG$_1$ subclass.

EXAMPLE II

Characterization of OKT1 Reactivity

A. Isolation of Lymphocyte Populations

Human peripheral blood mononuclear cells were isolated from healthy volunteer donors (ages 15-40) by FicollHypaque density gradient centrifugation (Pharmacia Fine Chemicals, Piscataway, N.J.) following the technique of Boyum, *Scand. J. Clin. Lab. Invest.* 21 (Supp. 97): 77, 1968. Unfractionated mononuclear cells were separated into surface Ig+ (B) and Ig- (T plus Null) populations by Sephadex G-200 anti-F(ab')$_2$ column chromatography as previously described by Chess, et al., *J. Immunol.* 113:1113 (1974). T cells were recovered by E rosetting the Ig- population with 5% sheep erythrocytes (Microbiological Associates, Bethesda, MD). The rosetted mixture was layered over Ficoll-Hypaque and the recovered E+ pellet treated with 0.155 M NH$_4$Cl (10 ml per 10$^8$ cells). The T cell population so obtained was >2% EAC rosette positive and <95% E rosette positive as determined by standard methods. In addition, the non-rosetting Ig- (Null cell) population was harvested from the Ficoll interface. This latter population was <5% E+ and ≦2% sIg+. The surface Ig+ (B) population was obtained from the Sephadex G-200 column following elution with normal human gamma globulin as previously described. This population was >95% surface Ig+ and <5% E+.

Normal human macrophages were obtained from the mononuclear population by adherence to polystyrene. Thus, mononuclear cells were resuspended in final culture media (RPMI 1640, 2.5 mM HEPES [4-(2-hydroxyethyl)-1-piperazinepropane sulfonic acid] buffer, 0.5% sodium bicarbonate, 200 mM L-glutamine, and 1% penicillin-streptomycin, supplemented with 20% heat-inactivated human AB serum) at a concentration of 2×10$^6$ cells and incubated in plastic petri dishes (100×20 mm) (Falcon Tissue Culture Dish; Falcon, Oxnard, CA) at 37° C. overnight. After extensive washing to remove non-adherent cells, the adherent population was detached by brisk washing with cold serum-free medium containing 2.5 mM EDTA and occasional scraping with the rubber tip of a disposable syringe plunger. Greater than 85% of the cell population was capable of ingesting latex particles and had morphologic characteristics of monocytes by Wright-Giemsa staining.

B. Normal Thymus

Normal human thymus gland was obtained from patients aged two months to 14 years undergoing corrective cardiac surgery. Freshly obtained portions of the thymus gland were immediately placed in 5% fetal calf serum in medium 199 (Gibco), finely minced with forceps and scissors, and subsequently made into single cell suspensions by being pressed through wire mesh. The cells were next layered over Ficoll-Hypaque and spun and washed as previously described in section A above. The thymocytes so obtained were >95% viable and ≧90% E rosette positive.

C. Cell Lines

Epstein-Barr Virus (EBV) transformed B cell lines from four normal individuals were prepared as previously described. T cell lines CEM, HSB-2, and HJD-1 were provided by Dr. H. Lazarus, Sidney Farber Cancer Institute, Boston, MA.

D. T Acute Lymphoblastic Leukemia (T-ALL) Cells and T Chronic Lymphatic Leukemia (T-CLL) Cells Leukemia cells were obtained from 12 patients with T-ALL. These individuals' cells had previously been determined to be of T cell lineage by their spontaneous rosette formation with sheep erythrocytes (>20% E+) and reactivity with T cell specific hetero-antisera, anti-HTL (anti-B.K.) and A99, as previously described by Schlossman, et al., *Proc. Nat. Acad. Sci.* 73:1288 (1976). Tumor cells from three individuals were reactive (TH$_2$+) with rabbit and/or equine anti-TH$_2$ while cells from the remaining nine were non-reactive (TH$_2$-). Leukemic cells from two patients with TH$_2$- T-CLL were also utilized. Both acute and chronic T cell leukemia cells were cryopreserved in −196° C. vapor phase liquid nitrogen in 10% dimethylsulfoxide and 20% AB human serum until the time of surface characterization. The tumor populations analyzed were >90% blasts by Wright-Giemsa morphology in all instances.

EXAMPLE III

Cytofluorographic Analysis and Cell Separation

Cytofluorographic analysis of all cell populations was performed by indirect immunofluorescence with fluorescein-conjugated goat-anti-mouse IgG (G/M FITC) (Meloy Laboratories) on a Cytofluorograf FC200/4800A (Ortho Instruments). In brief, 1-2×10$^6$ cells were treated with 0.15 ml OKT1 at a 1:1000 dilution, incubated at 4° C. for 30 minutes, and washed twice. The cells were then reacted with 0.15 ml of a 1:40 dilution G/M FITC at 4° C. for 30 minutes, centrifuged, and washed three times. These cells were then analyzed on the Cytofluorograf and the intensity of fluorescence per cell recorded on a pulse height analyzer. A similar pattern of reactivity was observed at a dilution of 1:30,000, but further dilution caused loss of reactivity. Background staining was obtained by substituting a 0.15 ml aliquot of 1:1000 ascites from a Balb/cJ mouse intraperitoneally immunized with a non-producing hybrid clone.

In experiments designed to separate OKT1+ and OKT1- cells, 100×10$^6$ unfractionated mononuclear cells or thymocytes were labeled with 4 ml of a 1:1000 dilution of OKT1 and developed with G/M FITC. An identical staining approach was utilized to prepare human T cells isolated as in Example IIA above. Utilizing a fluorescence activated cell sorter (FACS-I) (Becton-Dickinson, Mountain View, CA), lymphocytes were separated into OKT1+ and OKT1- populations and/or T cells were fractionated into weakly reactive OKT1+ T cells (lower 20% of fluorescence) and strongly reactive OKT1+ T cells (upper 20% of fluorescence). Post sort viability was >95% by Trypan blue exclusion in all instances. Purity of all separated populations was ≧95%.

EXAMPLE IV

Functional Studies

The mitogenic response of the unseparated and FACS fractionated lymphoid cells was tested in microculture to optimal doses of Concanavalin A (Con A) (Calbiochem, La Jolla, CA) and phytohemagglutinin (PHA) as previously described by Chess, et al. Alloantigen proliferative response was measured concurrently for these same populations using mitomycin treated Laz 156, an EBV transformed human B lymphoblastoid cell line obtained from Dr. H. Lazarus, as a stimulus. Proliferation to tetnus toxoid (Massachusetts Department of Public Health Biological Laboratories, Boston, MA) was tested as previously described by Evans, et al., (*J. Immunol.* 129: 1423, 1978), using a 10 μg/ml final concentration. Five percent macrophages obtained in the manner described above were added to all populations at the initiation of in vitro cultures. Mitogen stimulated cultures were pulsed after four days with 0.2 μCi of tritiated thymidine (1.9 Ci/mM specific activity; Schwartz-Mann Division of Becton-Dickinson, Orangeburg, NY) and harvested 18 hours later on a MASH II apparatus (Microbiological Associates, Bethesda, MD). Tritiated thymidine incorporation was measured in a Packard Scintillation Counter (Packard Instrument Company, Downer's Grove, IL). Background tritiated thymidine incorporation was obtained by substituting medium for mitogen. Tetnus toxoid- and alloantigen-stimulated cultures were pulsed after five days with tritiated thymidine for 18 hours, harvested, and counted as described above.

BRIEF DESCRIPTION OF THE DRAWINGS

FIG. 3 shows the fluorescence pattern obtained on the Cytofluorograf after reacting leukemic cells from both acute lymphoblastic leukemia and chronic lymphoblastic leukemia patients with OKT1 and G/M FITC.

FIG. 4 shows the fluorescence pattern obtained on the Cytofluorograf after reacting human T cell lines with OKT1 and G/M FITC.

FIG. 5 shows the fluorescence pattern obtained on the Cytofluorograf after reacting the B cell lymphoblastoid line Laz 007 with OKT1 and G/M FITC.

The production of the hybridoma and the production and characterization of the resulting monoclonal antibody were conducted as described in the above Examples. Although large quantities of the subject antibody were prepared by injecting the subject hybridoma intraperitoneally into mice and harvesting the malignant ascites, it is clearly contemplated that the hybridoma could be cultured in vitro by techniques well-known in the art and the antibody removed from the supernatant.

A sample of the subject hybridoma was deposited at the American Type Culture Collection, 12301 Parklawn Drive, Rockville, MD, 20852 on March 13, 1979, and has been assigned the ATCC number CRL 8000.

Figure 1:
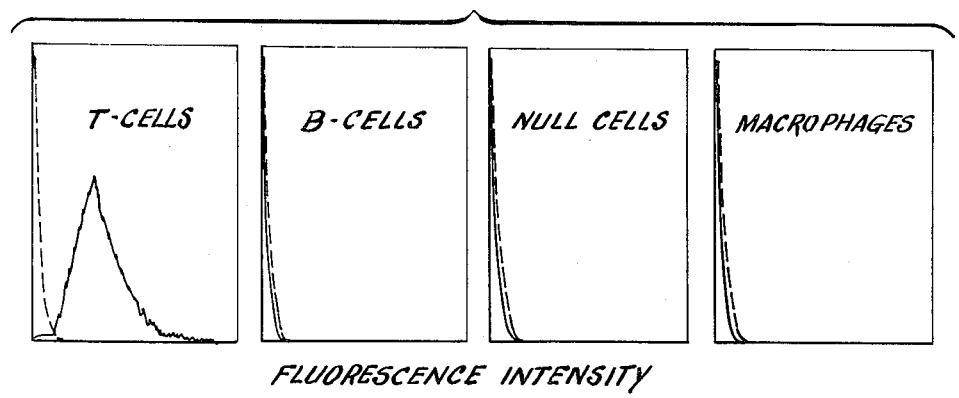
FIG. 1 shows the fluorescence pattern obtained on the Cytofluorograf after reacting the cell populations shown with OKT1 at a 1:1000 dilution and G/M FITC.

As shown in FIG. 1, the entire human peripheral blood T cell population of a given normal individual is reactive with OKT1, whereas the entire B cell, null cell, and macrophage populations isolated from the same individual are unreactive with OKT1. Similar results were obtained on populations of lymphocytes from fifteen other normal individuals. The monoclonal antibody is thus characterized in that it is reactive with an antigen contained on the surface of essentially all normal human peripheral T cells, while being unreactive with any antigens on the surface of the other three cell types shown in FIG. 1. This differential reactivity is one test by which the subject antibody OKT1 may be detected and distinguished from other antibodies.

Figure 2:
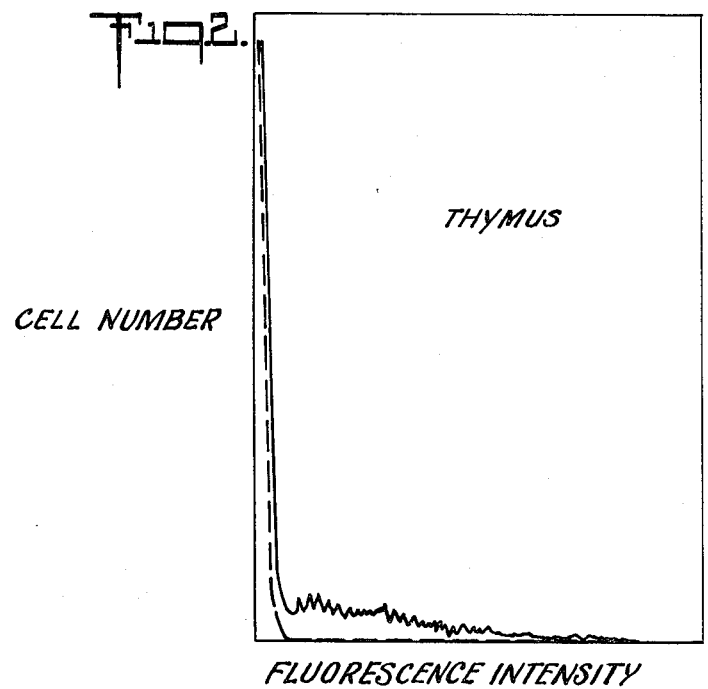
FIG. 2 shows the fluorescence pattern obtained on the Cytofluorograf after reacting human thymocytes with OKT1 and G/M FITC.

As shown in FIG. 2, the vast majority of normal human thymocytes from a six-month old infant are completely unreactive with OKT1, while about 5 to 10 percent of the thymocytes are reactive. The implication of this finding is that, during the differentiation process by which stem cells are converted into mature T cells, the thymocytes acquire at some stage the same surface antigen found on T cells, which is reactive with OKT1. It is believed that these thymocytes are in the later stages of differentiation just prior to emergence from the thymus into the bloodstream. Similar results (5-10% reactivity) were obtained using six additional thymus specimens from normal individuals two months to 19 years of age. The pattern of reactivity in FIG. 2 provides a second method of detecting the subject antibody OKT1 and distinguishing it from other antibodies.

A diagnostic use for the subject antibody is illustrated by FIG. 3, in which it is shown that leukemic cells from T acute lymphoblastic leukemia (T-ALL) patients were nonreactive with OKT1, whereas leukemic cells from T chronic lymphoblastic leukemia (T-CLL) patients were reactive with OKT1. The subject antibody therefore provides a method for distinguishing between these two forms of leukemia. Since it is difficult to distinguish between certain stages of T-ALL and T-CLL and since both the prognosis and the treatment regimen differ substantially between these two forms of leukemia, it can be seen that a straightforward method for distinguishing between the two provided by use of the subject antibody is a significant advance.

A further characterization of the subject antibody OKT1 is shown by the reactivity to various human T cell lines illustrated in FIG. 4. As can be seen, the reactivity of the subject antigen to human T cell lines was heterogeneous, being strong for the line HJD-1, moderate for the line CEM, and nonexistent for the line HSB-2. This differential reactivity of OKT1 to various readily-available human T cell lines provides yet another method of characterizing and describing the subject antibody.

FIG. 5 illustrates the lack of reaction of OKT1 with the human B cell line Laz 007. An identical pattern was obtained on the other EBV transformed B cell lines tested. This further supports the lack of reactivity of OKT1 with B cells obtained from the peripheral blood of a normal human population and provides yet another method for characterizing and distinguishing the subject antibody OKT1.

Functional studies were conducted on lymphoid populations which had been separated on a fluorescence activated cell separator (FACS). The results of these studies are shown in Tables I through III below and provide further support for the previously-described characterization of the subject monoclonal antibody.

As shown in Table I, essentially all of the responsiveness to PHA, Con A, soluble antigens, and alloantigen in mixed lymphocyte culture (MLC) resides in the population of cells responsive to OKT1. The population which was unreactive to OKT1 appeared to cause none of these T cell functions, the slight response being accounted for by possible contamination with OKT1+ cells. These functional studies are a further illustration that the antigen to which OKT1 is reacting resides only on T cells, since the population which is so reactive exhibits T cell functions, while the population which is not so reactive exhibits none of these functions. Table II illustrates that no functional differences in mitogen or alloantigen response exist between the strongly OKT1 reactive and weakly OKT1 reactive T cells separated on FACS. Both populations proliferated equally well and in a manner identical to the unfractionated T cell population. Table III suggests that the surface antigen with which OKT1 reacts is present only on mature thymocytes, since the activity of the entire range of thymocytes in the MLC assay is due almost entirely to that portion of the thymocyte population which is reactive with OKT1. Table III also shows the functional difference between OKT1+ lymphocytes and OKT1+ peripheral T cells, since the former lack mitogen responsiveness.

According to the present invention there are provided a hybridoma capable of producing antibody against an antigen found on essentially all normal human T cells, a method for producing this hybridoma, monoclonal antibody against an antigen found on essentially all human T cells, methods for producing the antibody, and methods for treatment or diagnosis of disease employing this antibody.

Although only a single hybridoma producing a single monoclonal antibody against human T cell antigen is described, it is contemplated that the present invention encompasses all monoclonal antibodies exhibiting the characteristics described herein. It was determined that the subject antibody OKT1 belongs to the subclass IgG$_1$, which is one of four subclasses of murine IgG. These subclasses of immune globulin G differ from one another in the so-called "fixed" regions, although an antibody to a specific antigen will have a so-called "variable" region which is functionally identical regardless of which subclass of immune globulin G it belongs to. That is, a monclonal antibody exhibiting the characteristic described herein may be of subclass IgG$_1$, IgG$_{2a}$, IgG$_{2b}$, or IgG$_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies.

Although the subject antibody is specifically IgG$_1$, it is contemplated that antibodies having the patterns of reactivity illustrated herein are included within the subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis of disease employing the monoclonal antibody OKT1 or any other monoclonal antibody exhibiting the pattern of reactivity provided herein. As discussed above, the subject antibody allows discrimination between T cell chronic lymphoblastic leukemia and T cell acute lymphoblastic leukemia and allows treatment of patients undergoing organ transplants to reduce or eliminate the rejection of these transplants.

TABLE I

FUNCTIONAL COMPARISON OF FACS-SEPARATED OKT1+ AND OKT1− PERIPHERAL LYMPHOCYTES

| Proliferative Stimulus | Whole Mononuclear | Whole Mononuclear OKT1 + G/M FITC Treated | OKT1+ | OKT1− |
|---|---|---|---|---|
| Con A | 146,032 ± 1,556 | 137,229 ± 3,600 | 133,557 ± 6,088 | 9,454 ± 1,080 |
| PHA | 32,001 ± 2,659 | 36,326 ± 3,311 | 29,877 ± 1,043 | 8,058 ± 869 |
| MLC | 122,958 ± 2,315 | 136,141 ± 1,056 | 148,235 ± 2,666 | 8,125 ± 1,033 |
| Tetanus Toxoid | 25,821 ± 4,132 | 28,756 ± 1,526 | 30,184 ± 563 | 2,124 ± 436 |
| Media Control | 482 ± 16 | 734 ± 65 | 533 ± 87 | 757 ± 108 |

TABLE II

FUNCTIONAL COMPARISON OF T CELLS STRONGLY REACTIVE AND WEAKLY REACTIVE WITH OKT1

| Proliferative Stimulus | Unfractionated T cells | Unfractionated T cells OKT1 + G/M FITC Treated | T cells strongly reactive with OKT1 | T cells weakly reactive with OKT1 |
|---|---|---|---|---|
| | | EXPERIMENT #1 | | |
| Con A | 59,499 ± 9,699 | 56,248 ± 3,057 | 64,656 ± 6,076 | 54,478 ± 5,173 |
| PHA | 116,062 ± 5,910 | 106,412 ± 5,348 | 112,246 ± 3,716 | 90,857 ± 5,500 |
| MLC | 95,261 ± 4,663 | 107,365 ± 12,001 | 119,605 ± 5,333 | 100,650 ± 8,215 |
| Media | 365 ± 22 | 399 ± 46 | 488 ± 23 | 402 ± 57 |
| | | EXPERIMENT #2 | | |
| Con A | 88,603 ± 2,133 | 104,241 ± 1,951 | 99,617 ± 7,213 | 117,672 ± 12,315 |
| PHA | 79,235 ± 2,615 | 65,803 ± 6,163 | 73,108 ± 2,226 | 67,159 ± 6,316 |
| MLC | 39,096 ± 5,776 | 35,929 ± 2,102 | 55,009 ± 8,333 | 42,165 ± 4,559 |
| Media | 157 ± 28 | 292 ± 6 | 322 ± 33 | 345 ± 25 |

TABLE III

FUNCTIONAL PROPERTIES OF HUMAN THYMOCYTE POPULATIONS

| Proliferative Stimulus | Unfractionated Thymocytes | Unfractionated Thymocytes OKT1 + G/M FITC Treated | OKT1+ Thymocytes | OKT1− Thymocytes |
|---|---|---|---|---|
| | | EXPERIMENT #1 | | |
| MLC | 7,085 ± 901 | 6,224 ± 823 | 6,556 ± 987 | 244 ± 10 |

TABLE III-continued

FUNCTIONAL PROPERTIES OF HUMAN THYMOCYTE POPULATIONS

| Proliferative Stimulus | Unfractionated Thymocytes | Unfractionated Thymocytes OKT1 + G/M FITC Treated | OKT1+ Thymocytes | OKT1− Thymocytes |
|---|---|---|---|---|
| Con A | 88 ± 10 | 94 ± 2 | 38 ± 2 | 36 ± 3 |
| PHA | 55 ± 6 | 78 ± 10 | 22 ± 2 | 51 ± 4 |
| Media | 40 ± 5 | 46 ± 10 | 10 ± 2 | 65 ± 11 |
| EXPERIMENT #2 | | | | |
| MLC | 3,815 ± 772 | 4,778 ± 623 | 5,727 ± 239 | 425 ± 81 |
| Con A | 46 ± 8 | 47 ± 10 | 100 ± 22 | 67 ± 32 |
| PHA | 66 ± 4 | 60 ± 4 | 142 ± 4 | 22 ± 4 |
| Media | 80 ± 15 | 67 ± 12 | 80 ± 18 | 200 ± 16 |

What is claimed is:

1. A monoclonal antibody of class IgG produced by a hybridoma formed by fusion of cells from a mouse myeloma line and spleen cells from a mouse previously immunized with human T cells, which antibody:
   (a) reacts with essentially all normal human peripheral T cells but not with normal human peripheral B cells, null cells or macrophages;
   (b) reacts with from about 5% to about 10% of normal human thymocytes;
   (c) reacts with leukemic cells from humans with T cell chronic lymphoblastic leukemia but does not react with leukemic cells from humans with T cell acute lymphoblastic leukemia;
   (d) exhibits a pattern of reactivity with the human T cell lines HJD-1, CEM, and HSB-2 shown in FIG. 4; and
   (e) does not react with Epstein-Barr virus-transformed human B cell lines.

2. The monoclonal antibody of claim 1 which is of subclass $IgG_1$.

3. The monoclonal antibody of claim 1 which is produced from a hybridoma formed by fushion of P3X63AgU1 myeloma cells and spleen cells from a Balb/cJ mouse previously immunized with E rosette purified human T cells.

4. A monoclonal antibody of class IgG produced by a hybridoma formed by fusion of cells from a mouse myeloma line and spleen cells from a mouse previously immunized with human T cells which reacts with essentially all normal human peripheral T cells but not with normal human peripheral B cells, null cells, or macrophages.

5. Mouse monoclonal antibody which reacts with essentially all normal human peripheral T cells but not with normal human peripheral B cells, null cells, or macrophages.

6. A monoclonal antibody which reacts with essentially all normal human peripheral T cells but not with normal human peripheral B cells, null cells, or macrophages, prepared by the method, which comprises the steps of:
   (i) immunizing mice with E rosette positive purified human T cells;
   (ii) removing the spleens from said mice and making a suspension of the spleen cells;
   (iii) fusing said spleen cells with mouse myeloma cells in the presence of a fusion promoter;
   (iv) diluting and culturing the fused cells in separate wells in a medium which will not support the unfused myeloma cells;
   (v) evaluating the supernatant in each well containing a hybridoma for the presence of antibody to E rosette positive purified T cells;
   (vi) selecting and cloning a hybridoma producing antibody which reacts with essentially all normal human peripheral T cells but not with normal human peripheral B cells, null cells, or macrophages; and
   (vii) recovering the antibody from the supernatant above said clones.

7. A monoclonal antibody which reacts with essentially all normal human peripheral T cells but not with normal human peripheral B cells, null cells, or macrophages prepared by the method, which comprises the steps of:
   (i) immunizing mice with E rosette positive purified human T cells;
   (ii) removing the spleens from said mice and making a suspension of the spleen cells;
   (iii) fusing said spleen cells with mouse myeloma cells in the presence of a fusion promoter;
   (iv) diluting and culturing the fused cells in separate wells in a medium which will not support the unfused myeloma cells;
   (v) evaluating the supernatant in each well containing a hybridoma for the presence of antibody to E rosette positive purified T cells;
   (vi) selecting and cloning a hybridoma producing antibody which reacts with essentially all normal human peripheral T cells but not with normal human peripheral B cells, null cells, or macrophages;
   (vii) transferring said clones intraperitoneally into mice; and
   (viii) harvesting the malignant ascites or serum from said mice, which ascites or serum contains the desired antibody.

8. A method of preparing monoclonal antibody which reacts with essentially all normal human peripheral T cells but not with normal human peripheral B cells, null cells, or macrophages, which comprises culturing the hybridoma ATCC CRL 8000 in a suitable medium and recovering the antibody from the supernatant above said hybridoma.

9. The monoclonal antibody prepared by the method of claim 8.

10. A method of preparing monoclonal antibody which reacts with essentially all normal human peripheral T cells but not with normal human peripheral B cells, null cells, or macrophages, which comprises injecting into a mouse the hybridoma ATCC CRL 8000 and recovering the antibody from the malignant ascites or serum of said mouse.

11. The monoclonal antibody prepared by the method of claim 10.

* * * * *